United States Patent [19]

Stuckey

[11] Patent Number: 5,400,640
[45] Date of Patent: Mar. 28, 1995

[54] PYROTECHNIC SHOCK MACHINE

[75] Inventor: Raymond L. Stuckey, Manassas, Va.

[73] Assignee: International Business Machines Corporation, Armonk, N.Y.

[21] Appl. No.: 142,995

[22] Filed: Oct. 29, 1993

[51] Int. Cl.$^6$ .............................................. G01L 1/00
[52] U.S. Cl. .................................... 73/12.14; 73/12.13
[58] Field of Search ................. 73/12.03, 12.04, 12.09, 73/12.14, 575, 576, 12.13; 181/114, 121

[56] References Cited

U.S. PATENT DOCUMENTS

| | | | |
|---|---|---|---|
| 2,799,824 | 8/1957 | Heynick et al. | |
| 3,393,763 | 7/1968 | Sundt | 181/114 |
| 3,557,603 | 1/1971 | Carr | |
| 3,659,456 | 5/1972 | Marshall et al. | 73/664 |
| 3,842,661 | 10/1974 | Marshall et al. | 73/664 |
| 4,118,994 | 10/1978 | Layotte et al. | 181/121 |
| 4,244,437 | 1/1981 | Fulkerson | 181/114 |
| 4,546,654 | 10/1985 | Isherwood et al. | |
| 4,609,066 | 9/1986 | Layotte et al. | 181/114 |
| 5,003,811 | 4/1991 | Shannon et al. | 73/12.14 |
| 5,048,320 | 9/1991 | Mitsuhashi et al. | 73/12.09 |

FOREIGN PATENT DOCUMENTS

| | | | |
|---|---|---|---|
| 913098 | 3/1982 | U.S.S.R. | 73/12.14 |
| 1458747 | 12/1986 | U.S.S.R. | 73/12.04 |

Primary Examiner—Richard E. Chilcot, Jr.
Assistant Examiner—R. Biegel
Attorney, Agent, or Firm—John D. Flynn; Joseph C. Redmond, Jr.

[57] ABSTRACT

A pyrotechnic shock testing machine employs flexure plates attached to an anvil lying in a vertical plane of a supporting frame to apply pyrotechnic shock pulses to a test unit attached to the anvil when a hammer is dropped to strike the anvil. The dimensions of the flexure plates can be selected to control the lower frequencies of the shock pulse. The anvil materials and their coupling can be selected to control the higher frequencies of the shock pulse whereby shock pulses in the range of 100 to 10000 hertz and accelerations in the range of 50 to 10000 g's can be applied to a test unit in the x, y and z directions. The shock testing apparatus is compact and portable and without the need to have complex hammer raising and dropping mechanisms.

15 Claims, 17 Drawing Sheets

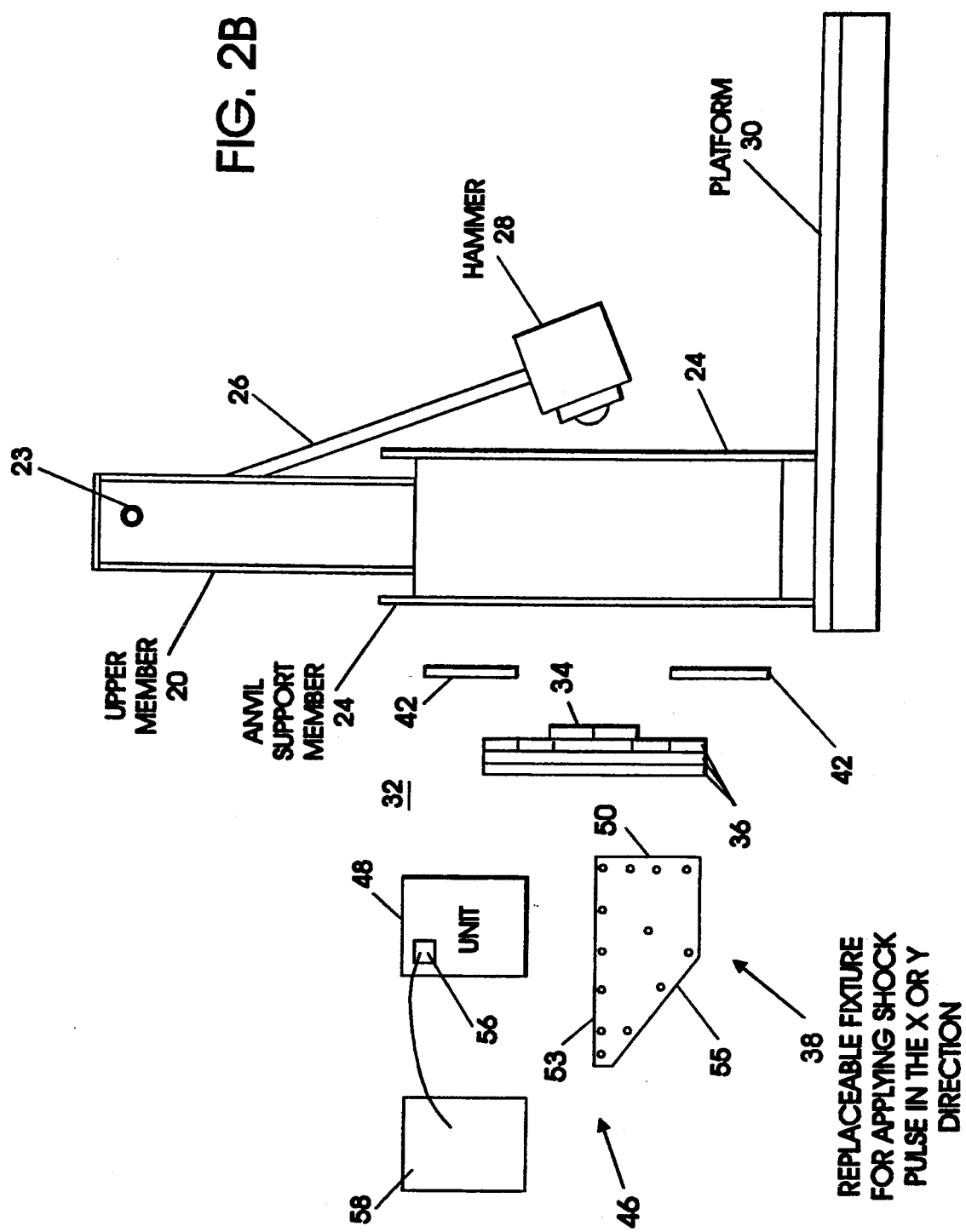

ACCEL 1, LEFT CENTER

ACCEL 1,
LEFT CENTER

ACCEL 2,
TOP RIGHT CORNER

ACCEL 2,
TOP RIGHT CORNER

+ PRIMARY POSITIVE
○ PRIMARY NEGATIVE

RIGHT SIDE CENTER

RIGHT SIDE CENTER

RIGHT SIDE CENTER

TOO LOW - NOT ACCEPTABLE
RIGHT SIDE CENTER

LEFT FRONT CORNER
(CONNECTOR SIDE)

LEFT FRONT CORNER (CONNECTOR SIDE)

+ PRIMARY POSITIVE
□ PRIMARY NEGATIVE $$fn = 3700\sqrt{\frac{t^3}{w}}$$

$$\therefore \quad t = \sqrt[3]{\frac{fn^2 w}{1370 \times 10^6}}$$

T = IS THE THICKNESS OF 10 INCH WIDE FLEXTURES (in.)
w = TOTAL WEIGHT SUPPORTED BY THE FLEXTURES (lb.)
W = TOTAL WEIGHT OF UNIT WITH FIXTURE (lb.)

PYROTECHNIC SHOCK MACHINE

BACKGROUND OF THE INVENTION

1. Technical Field

This invention relates to measuring and testing apparatus and methods therefor. More particularly, the invention relates to shock testing apparatus and methods of operation designed to stimulate pyrotechnic shock (high g accelerations short duration) conditions.

2. Description of Related Art

Pyrotechnic shock testing involves applying high energy forces to electronic or mechanical components or subsystems prior to installation in commercial or military equipment. The forces provide the component with accelerations of as high as 50000 g's, g being the acceleration constant of gravity, in less than several milliseconds. The forces may be recorded in a Time-History (TH) diagram which plots acceleration or g's versus time. TH diagram may be transformed into a Shock Response Spectrum (SRS) which plots the shock response, in g's versus frequency, in hertz.

Pyrotechnic testing apparatus should provide predictable, repeatable and controllable SRS profiles, in particular the frequency components of the shock should be within a selected db tolerance, typically + or −3 db or 6 db for both positive and negative shock response. The testing apparatus should also be able to provide a wide range of g accelerations, in some cases as high as 10000 g's. Preferably, the test apparatus should be simple to operate, compact, transportable and without complex hammer lifting and dropping mechanisms.

Pyrotechnic shock testers can be electrodynamic shakers or drop testers or employ explosives. Electrodynamic shakers have limiting input forces and generally provide SRS profiles up to 2000 g's and 5000 hertz. Drop testers provide acceptable SRS profiles up to 6000 g's, but only in the positive direction. Explosive using testers are acceptable for 5000 g's and higher, but have their own obvious problems.

In the prior art, U.S. Pat. No. 2,799,824 discloses a shock testing device which does not provide any method to effect a change in the input frequency of the shock. U.S. Pat. No. 3,557,603 discloses a shock machine which is characterized by low acceleration levels (less than 200 g's), low frequencies (less than 200 hertz) and very low, constant deceleration levels (less than 6 g's). U.S. Pat. No. 5,003,811 discloses shock testing apparatus which provides SRS profiles approaching 10000 g's and 10000 Hertz through the use of complex beam balancing techniques to achieve desired SRS profiles for the component under test. Overall, none of the prior art apparati are compact and suitable for portability. In particular, the '811 patent describes shock testing apparatus which is at least 77 inches long, and consequently not readily transportable. Likewise, the extensive structural arrangement and weight of the prior art apparati limit their compactness and transportability.

SUMMARY OF THE INVENTION

An object of the invention is a compact, portable pyrotechnic shock machine or tester which provides predictable, repeatable SRS profiles.

Another object is a pyrotechnic shock tester which facilitates altering the low and high frequencies of the SRS profile to a test unit for testing in the x, y and z directions.

Another object is a pyrotechnic shock tester which provides both the positive and negative acceleration in time-history (TH) to meet both positive and negative SRS requirements.

Another object is a method of operating a pyrotechnic shock tester to achieve SRS profiles up to 10000 g's and 10000 hertz.

A feature of the invention is the orientation of the anvil in the vertical plane of the shock tester frame which minimizes the tester's size and contributes to the portability of the present invention relative to the prior art.

These and other objects and features of the invention are accomplished by a frame which is mounted on a transportable base and includes a pendulum and hammer mechanism. The mechanism includes means for marking the drop point of the hammer to achieve repeatable hammer acceleration rates. The frame further includes a support means for an anvil mounted to the support means by flexure plates, the size, width and thickness of the flexure plates controlling the low frequency components of the SRS profile. The anvil comprises a plurality of plates which control the high frequency components of the SRS profile. The plate materials may be selected to assure ringing or dampening of a shock pulse. Attached to the anvil is a replaceable fixture for supporting a test unit. One fixture permits a shock pulse to be applied to the test unit in a z direction. Another fixture permits a shock pulse to be applied to the test unit in the x or y direction. Accelerometers are attached to the test unit and shock pulses provided to the test unit, the accelerometer outputs being supplied to a conventional digital acquisition/analysis system. The system provides TH and SRS profiles of the test unit as the hammer is caused to strike the anvil.

To operate the tester, the number, thickness and configuration of the flexure plates are calculated using a nomograph to achieve a desired resonant frequency of the SRS profile. The flexure plates are installed in the supporting frame. The anvil is connected to the flexure plates. The anvil includes a plurality of plates, one of which is a striking plate installed in the frame to be in the path of the hammer when it is dropped from a preselected drop point. The thicknesses and material of the other plates are selected to control the stiffness of the anvil and the high frequency response of the tester.

A replaceable fixture is attached to the anvil, one for testing in the z direction and the other for testing in the x and y directions. Depending on the required SRS profile, the fixtures can increase or decrease the tester resonance depending on how they are attached and coupled to the anvil plates loosely (isolated), with spacers or directly. The test unit is attached to the replaceable fixture according to the desired testing. Accelerometers are connected to the test unit and the accelerometer outputs supplied to a digital data acquisition/analysis system.

To generate a TH and SRS profile in the z direction for the test unit, the replaceable fixture is attached to the anvil, such that the test unit is in a plane perpendicular to the hammer striking angle. To generate a TH and SRS profile in the x direction for the test unit, the replaceable fixture is attached to the anvil, such that the test unit is in a plane parallel to the angle the hammer strikes the anvil. To generate a TH and SRS profile in a y direction, the test unit is rotated 90 degree on the replaceable fixture attached to the anvil for conducting the x direction shock test. The design of the replaceable fixtures is such that the low frequency response of the fixtures are similar. When testing a unit, the configuration of the flexure plates need not be changed for testing a unit in the x, y and z directions.

DESCRIPTION OF THE DRAWING

FIG. 2B is an exploded side view of the apparatus shown in FIG. 2A.

DESCRIPTION OF THE PREFERRED EMBODIMENT

Figure 1A:
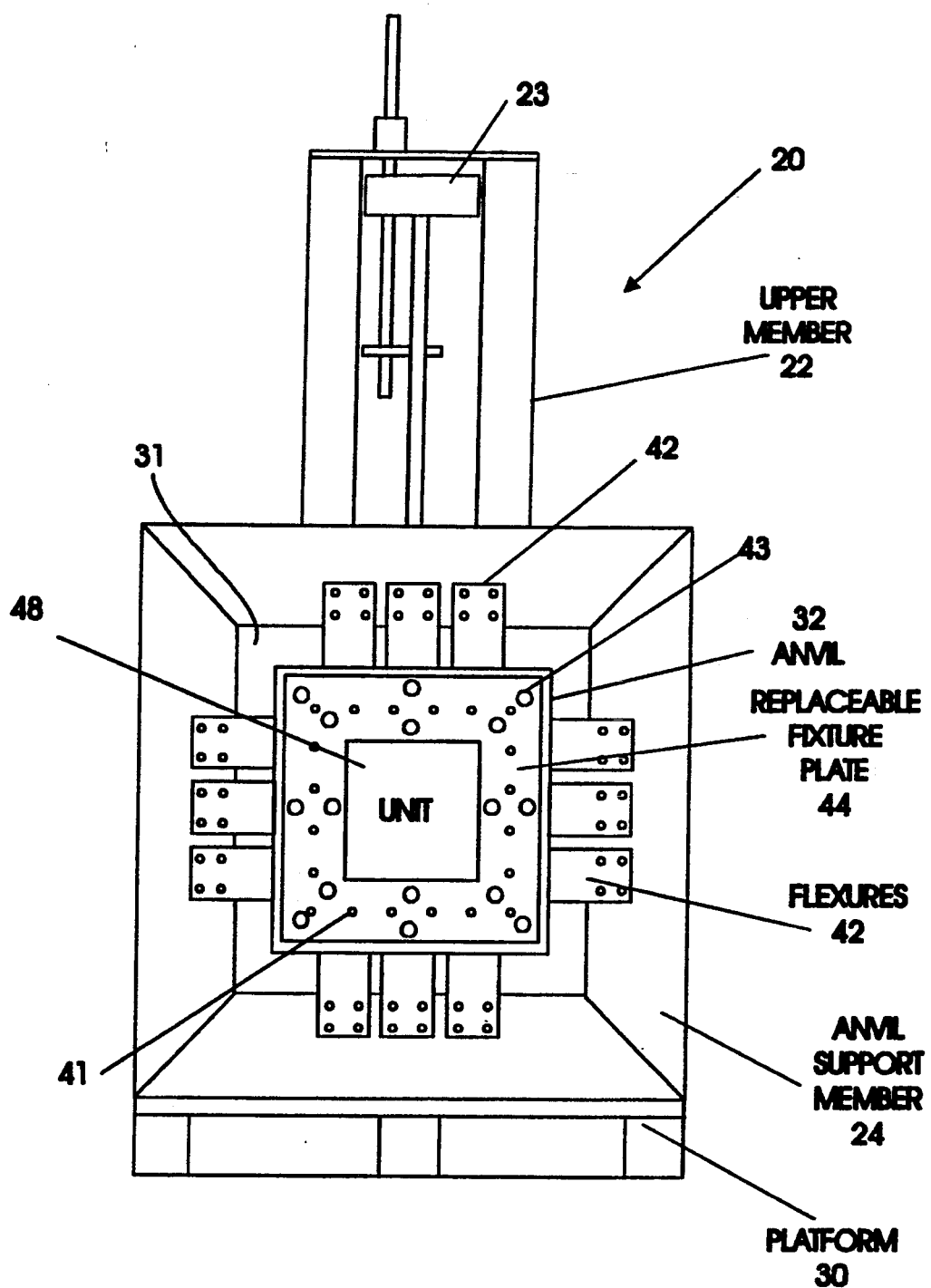
FIG. 1A is a front view of pyrotechnic shock testing apparatus which incorporates the present invention for testing a component in its z direction.
Figure 1B:
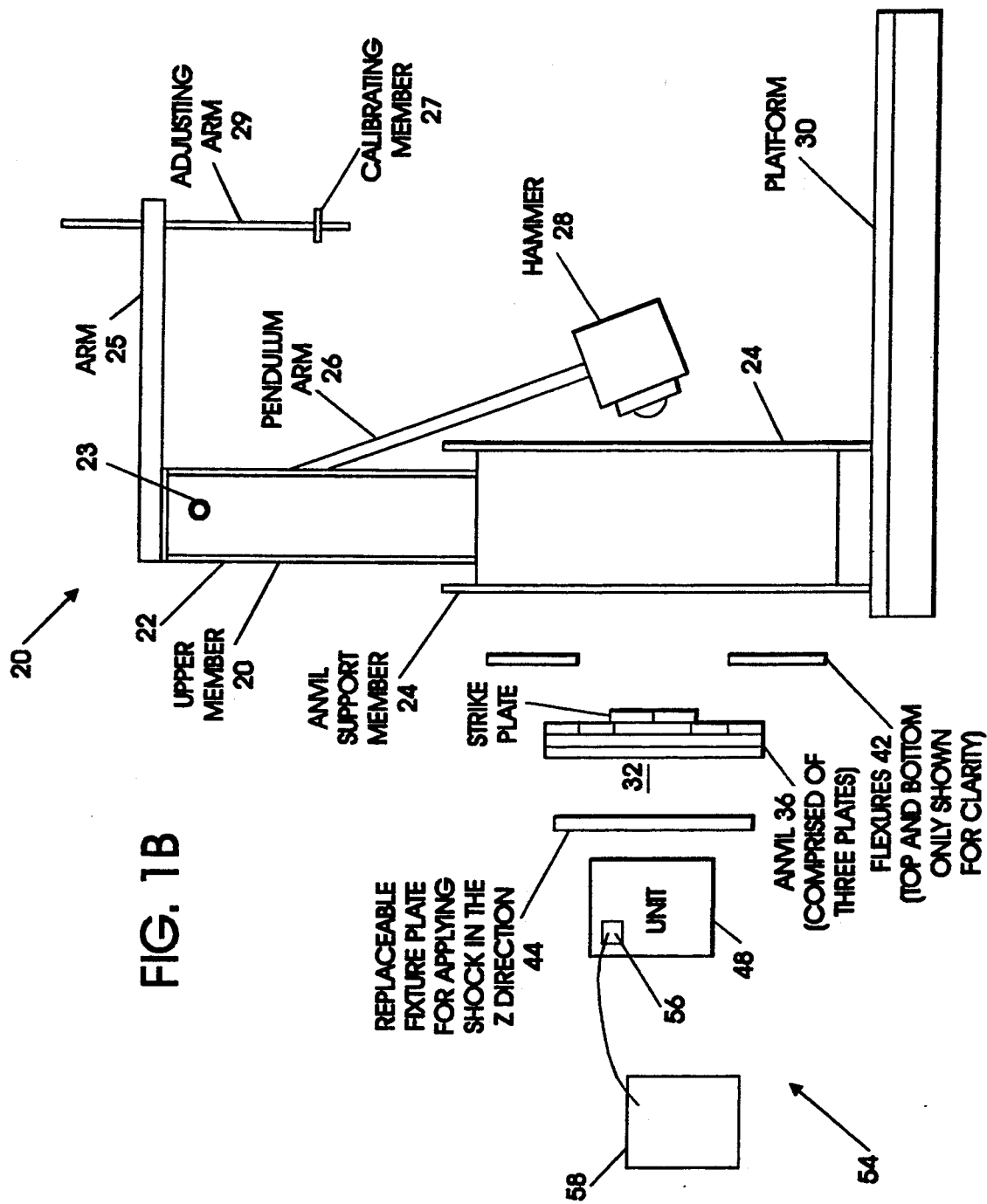
FIG. 1B is an exploded side view of the apparatus shown in FIG. 1A.

In FIGS. 1A and 1B, a vertical frame 20 is assembled from 10 by 5 inch steel "I" beams, and includes an upper member 22 and an anvil support member 24. The upper member 22 includes spaced channels connected together by a pendulum support mechanism 23. The mechanism 23 includes a pendulum arm 26 and a hammer 28, which in one embodiment may weigh 50 pounds. An arm 25 extends rearwardly from the mechanism 23 and in line with the path of the pendulum. A calibrating member 27 travels on an adjusting arm 29 and is adapted to be raised and lowered within the travel path of the pendulum to set the height at which the hammer is released to apply shock to a component or unit under test. While the hammer raising and dropping are manually controlled it is evident from the prior art that the raising and lowering of the hammer could be done electromechanically or otherwise.

Figure 1C:
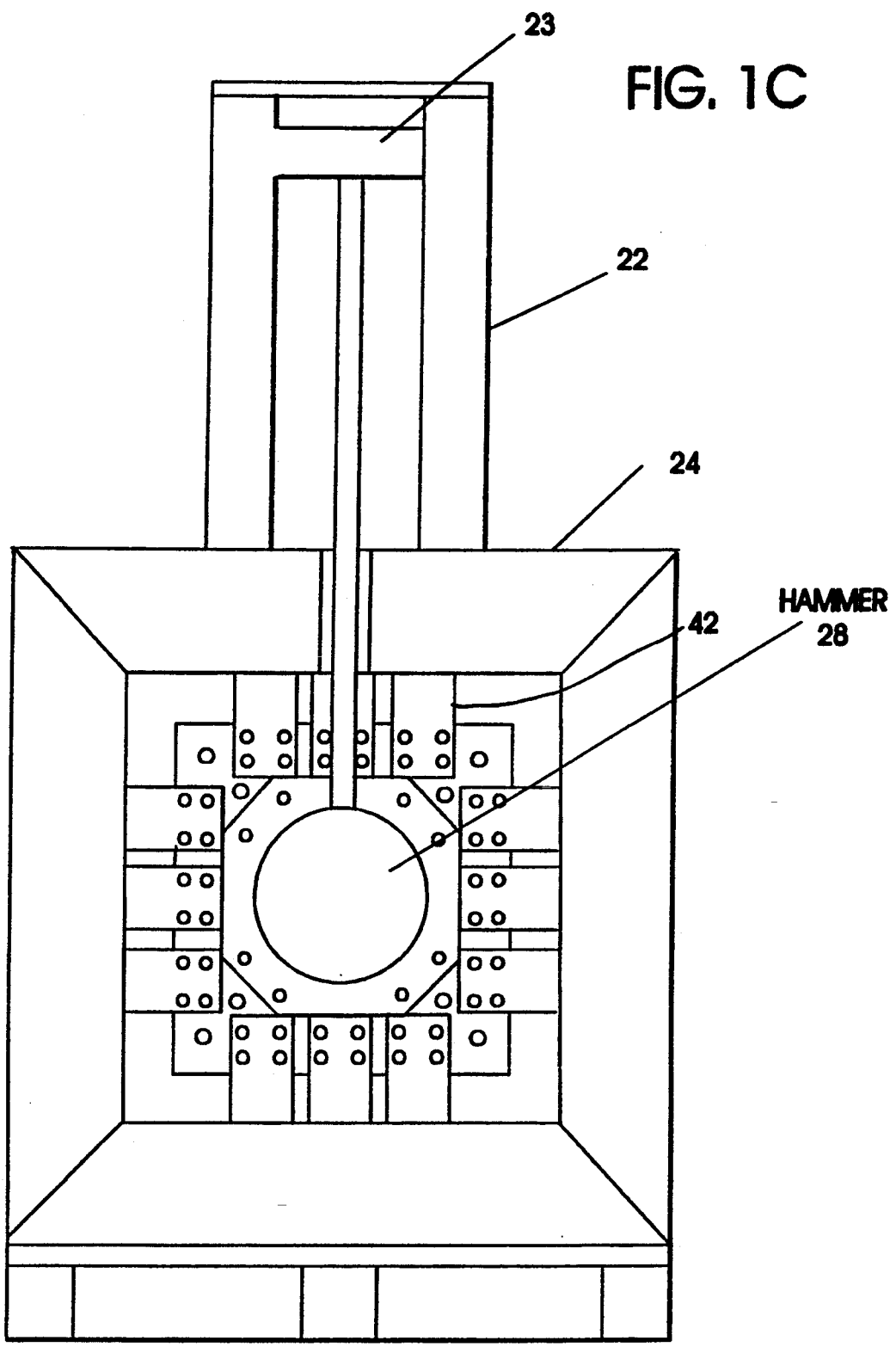
FIG. 1C is a rear view of the apparatus shown in FIG. 1A.

The upper member 22 is joined to the anvil support member 24, as shown in FIG. 1B. The support member 24 comprises "I" beam sections arranged in a square configuration, the lower element of the support member being joined to a transportable platform 30, such that the entire frame assembly can be picked up with a pallet truck or the like. The height of the frame is approximately 48 inches. The weight of the frame and other elements to be described are approximately 700 pounds which can be readily picked up by the pallet truck and transported to a desired test location. The upper member 22 and the support member 24 are configured and joined together such that the pendulum and hammer may freely swing within them, as shown in FIG. 1C.

Returning to FIGS. 1A and 1B, an anvil 32 is assembled for suspension within a square opening 31 of the support member 24. The anvil comprises a strike plate 34, which may be of steel or other hardened material to withstand the repeated impact of the hammer. Typically, the dimensions of the plate are 4 inches square and 1.0 inches thick. The strike plate is bolted to a plurality of anvil plates 36, typically three (3) plates which may be of steel or other like material to transmit the shock to the component under test. The plates may be selected to transmit or dampen the shock to the component under test according to the desired high frequency components of the SRS profile. The dimensions of the anvil plates are approximately 14 inches square and 2 inches thick overall. The strike plate and anvil plates 36 are bolted together to complete the anvil assembly by means of a set of openings (not shown) contained therein. The anvil plates contain a second set of openings 41 which will be described hereinafter in connection with attaching replaceable fixtures 44 and 46 to the anvil plates. The periphery of the anvil plates contains through holes for receiving bolt members (not shown) to join one end of two or more flexure plates 42 to the anvil. The other end of the flexure plates is fastened, e.g., bolted to the anvil member. In one embodiment, the number of flexure plates was 12 distributed equally among the sides of the anvil plates. The dimensions of each flexure plate were 2.5 inches wide, 6 inches long and with a thickness of 0.6 inches. Details on calculating the number and thickness of the flexure plates will be described in connection with FIGS. 7A and 7B. It should be noted that the anvil including the flexure plates lie in the vertical plane of the testing apparatus not the horizontal plane of the test apparatus, as in the prior art, which renders the present invention more compact and transportable than prior art shock testing apparatus. Completing the test apparatus are replaceable fixture elements 44 and 46 (see FIGS. 1 B and 2B), which support a component or a test unit 48 under test.

In FIGS. 1A and 1B, the fixture 44 is a metallic plate, typically steel or other material for transmitting the shock to the component in the z direction. The fixture includes threaded holes 41 for bolting the component or test unit 48 to the fixture to withstand the shock transmitted from the hammer striking the anvil. The fixture 44 includes through holes 43 for bolting to the openings (not shown) contained in the anvil plates 36. The test unit 48 is connected to measuring means 54 including an accelerometer 56 and a digital data acquisition and analysis system 58.

Figure 2A:
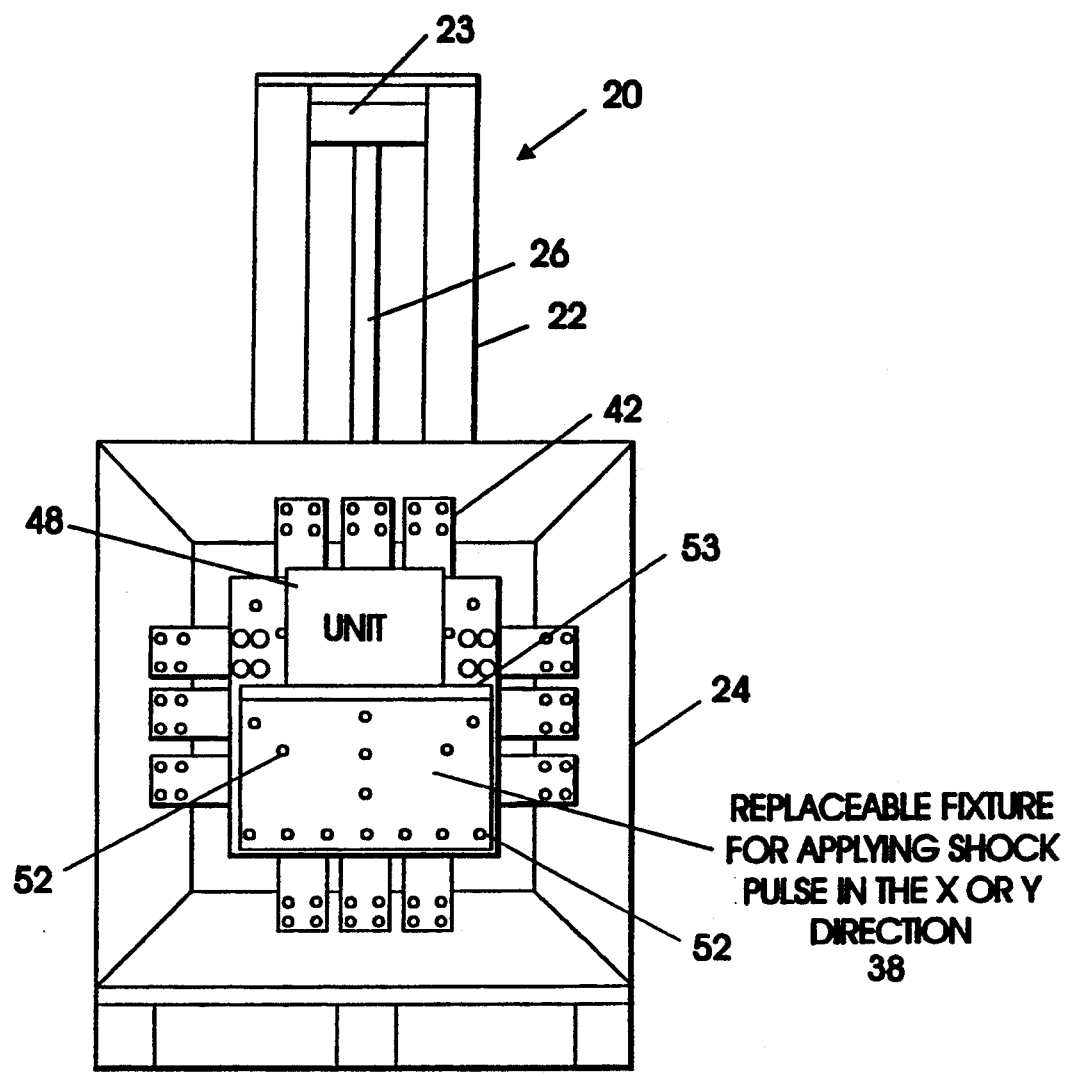
FIG. 2A is a front view of the pyrotechnic shock testing apparatus of FIGS. 1A and 1B for testing a component in its x and y directions.

Referring to FIGS. 2A and 2B, the replaceable fixture 46 for testing in the x and y directions includes a base plate 50 which has through holes 52 for bolting to the anvil plates 36. Attached to the base plate 50 is a right angle plate 53 with two gusset plates 55. The plate 53 includes threaded holes (not shown) for holding the component or test unit against the shock while undergoing testing in the x or y direction. The test unit 48 is tested in one position and rotated 90 degrees on the plate 53 for testing in the other direction under test.

To prepare the tester of the present invention for operation, the accelerometers 56 are installed on the test unit at various points. The accelerometers 56 are commercially available, such as Endevco Number 2225. The accelerometers are connected to a conventional digital data acquisition and analysis system 58, such as Prosig Conquest which includes a digital data acquisition and analysis program. When the test apparatus of the present invention is operated as will be described hereinafter, TH and SRS profiles will be generated as shown in FIGS. 3A through 6B.

Figure 7A:
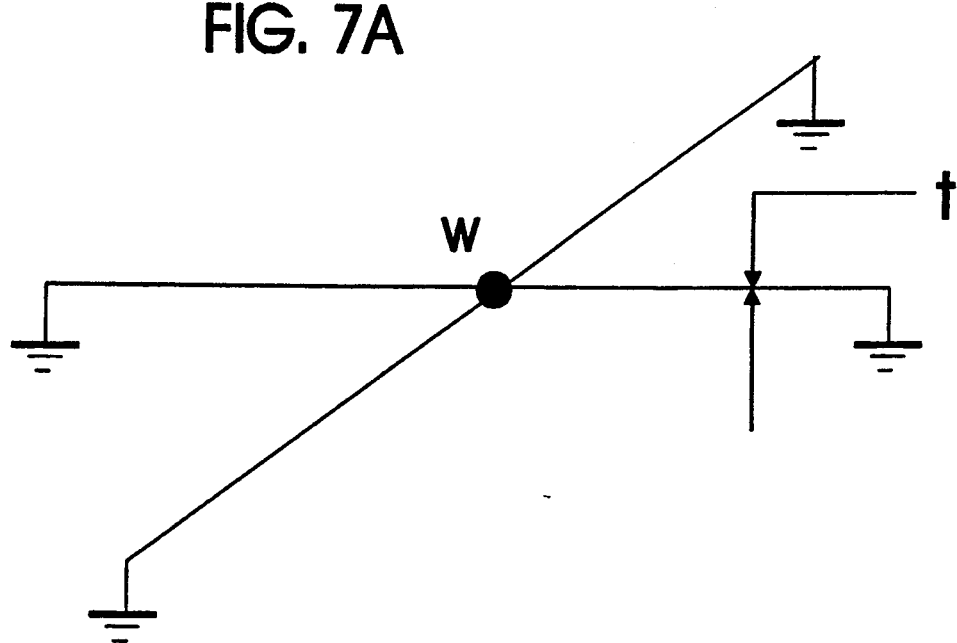
FIG. 7A is a diagram of the test apparatus for deriving an equation relating flexure plate thickness to shock frequencies using standard beam calculations.

Before operating the test apparatus of the present invention, the number and dimensions of the flexure plates may be determined from the equation shown in FIG. 7A. The equation was derived from standard beam calculations using the principles described in the text "Formula for Stress and Strain" by Raymond J. Roark, published by McGraw Hill 1965. In the equation shown in FIG. 7A, the terms are as follows:

$t$ = Thickness of the flexure plate in inches.
$W$ = Weight of the anvil and test fixture in pounds.
$f$ = Resonant frequency of a flexure/mass in hertz.
$k$ = A coefficient equal to 37000 calculated for the test system of the present invention, according to the cited text.

Figure 7B:
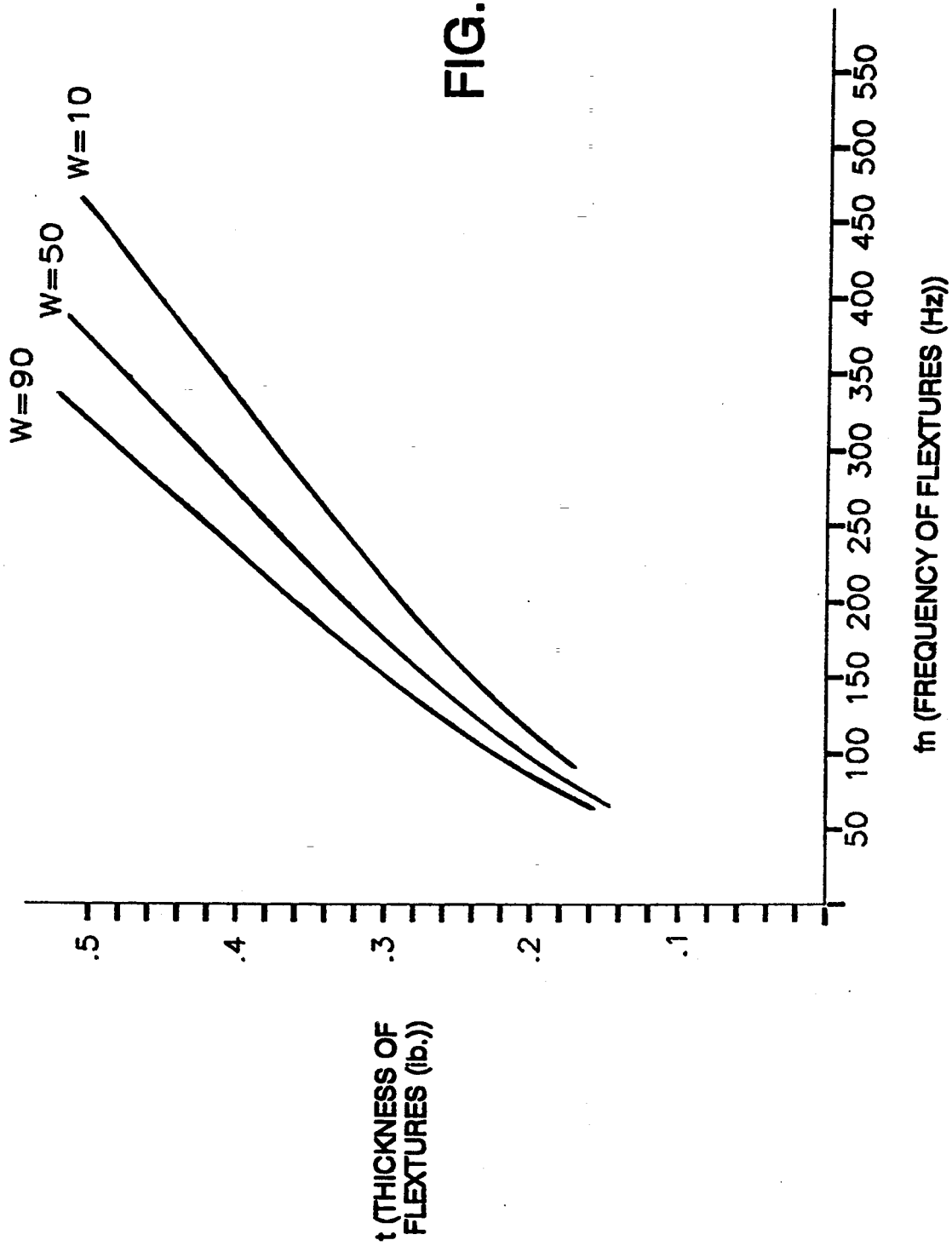
FIG. 7B is a nomograph of flexure plate thickness versus its frequency for various weights of the anvil and component under test based on calculations using the equation of FIG. 7A.

The nomograph of FIG. 7B shows that for a flexure plate that is 10 inches wide with a length of 2.0 inches on each side of the anvil plates and where the weight (w) equals 50 pounds, the thickness of the plates is about 0.3 inches to create a resonant frequency of 180 hertz. From experience, the highest frequency of the flexures is approximately 500 hertz because of deflections in the "I" beam structure. The structure could be stiffened to increase the highest flexure resonance. Also, the lowest practical flexure frequently is of the order of 150 hertz to keep the flexures from deforming too much.

To conduct a pyrotechnic shock test on a component or test unit in the z direction using the flexure plates of FIG. 7B, the following steps are observed:

Step 1: The test unit 48 is clamped to the replaceable fixture 44 which is bolted to the anvil plates 36, as shown in FIGS. 1A and 1B.

Step 2: An accelerometer is attached to the left center of the test unit 48.

Step 3: The drop height of the hammer is selected and the calibrating element 27 extended to contact the arm 26 to establish a drop point for the hammer.

Step 4: The hammer is physically raised to the drop point and released to apply a shock to the test unit.

Step 5: The TH and SRS profiles are generated by the digital acquisition and analysis system as shown in FIGS. 3A and 3B, for the left center of the test unit.

Step 6: The +/−3 db tolerance of the SRS profile can be controlled at the low frequencies by varying the thickness of the flexure plates. The upper frequencies of the SRS profile can be controlled by altering the stiffness of the anvil through the selection of materials, e.g., steel versus aluminum, etc., and the tightness of coupling the anvil plates.

Figure 3A:
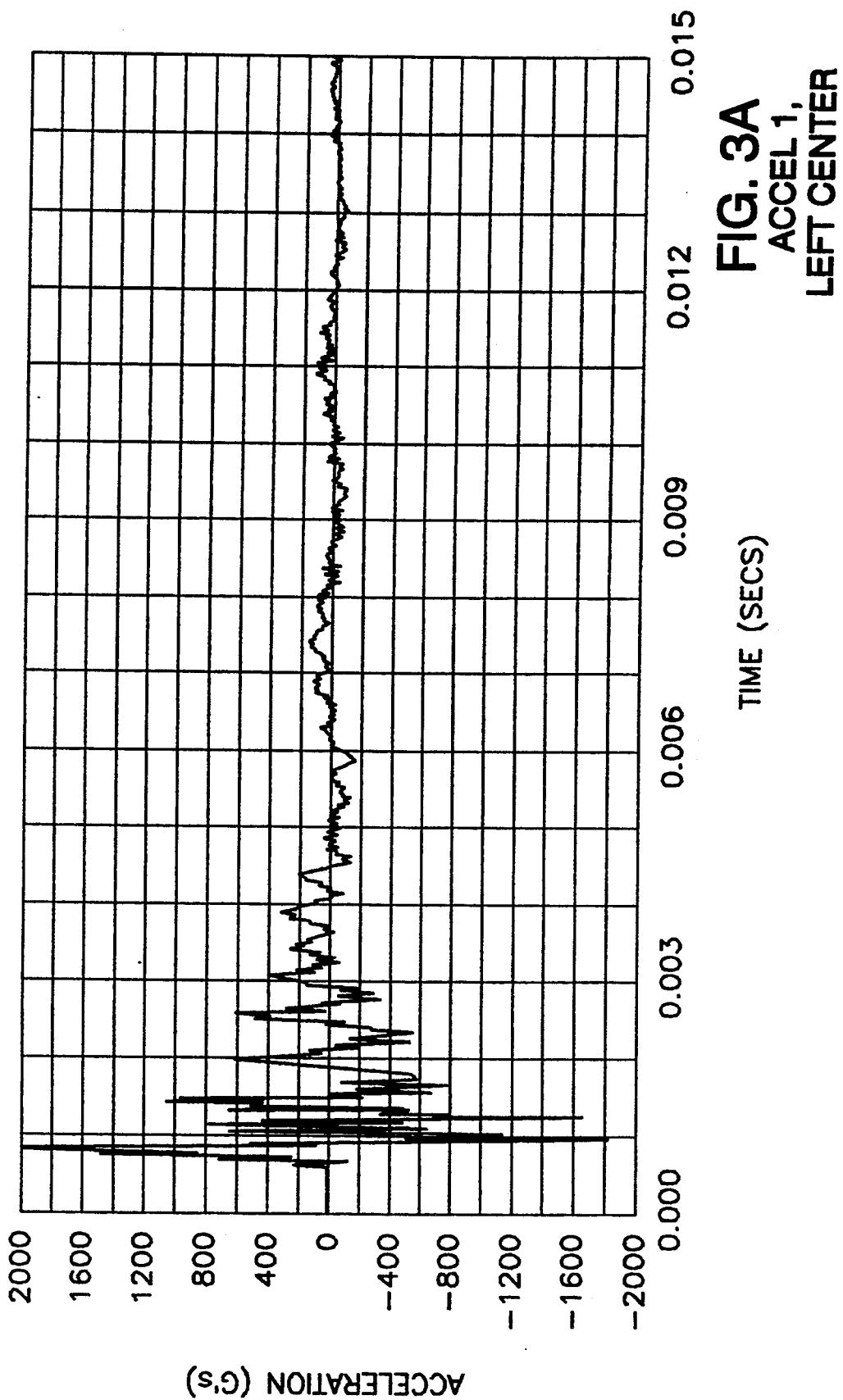
FIG. 3A is a TH profile for the component tested at its left center in the z direction.
Figure 3B:
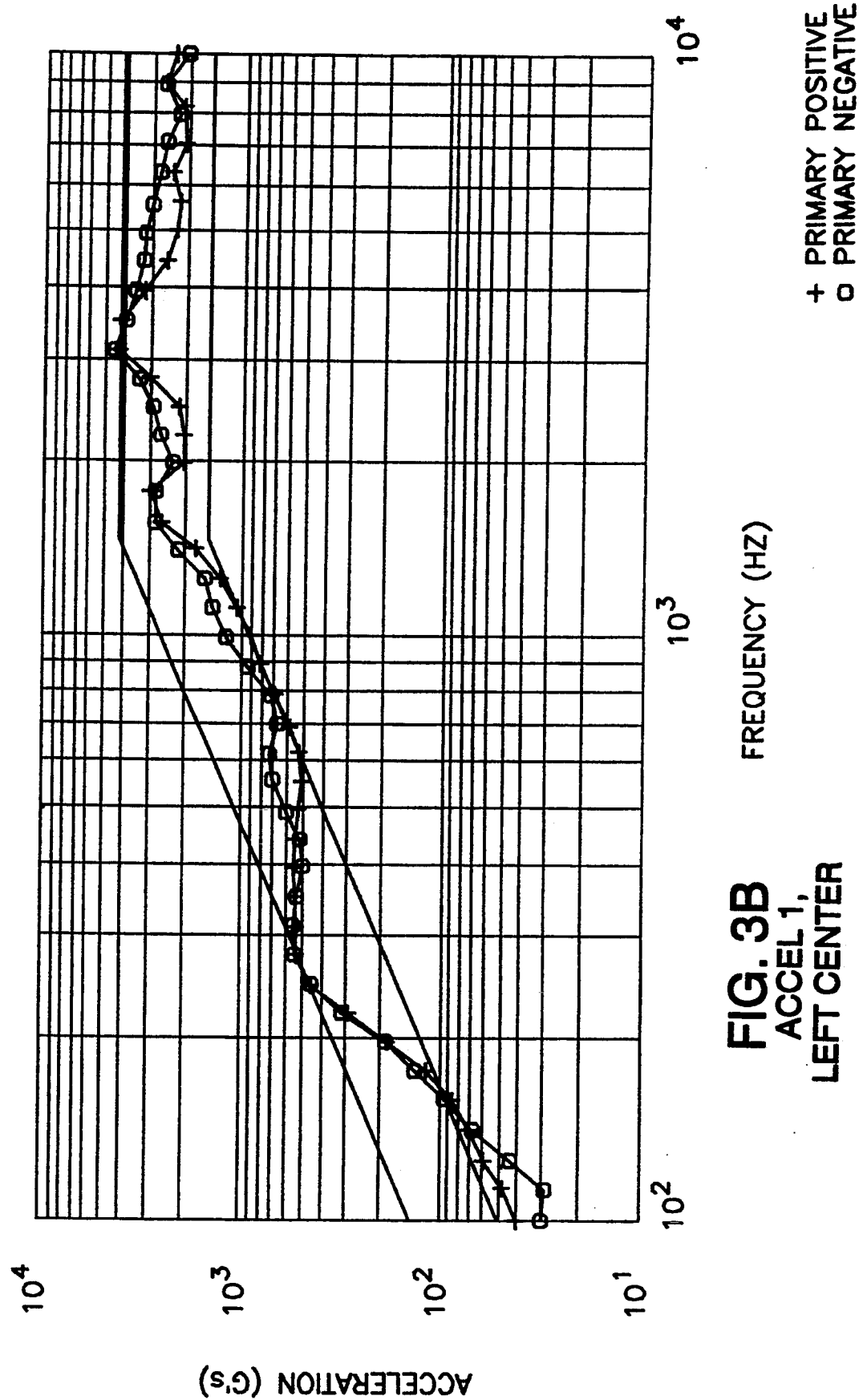
FIG. 3B is a SRS profile of the component tested at its left center in the z direction.

In FIG. 3B, the SRS profile for the unit under test is within the +3/−6 db tolerance range as evident by the primary positive and primary negative points along the profile. FIG. 3B demonstrates that the shock testing apparatus of the present invention can achieve a frequency range of 100 to 10000 hertz for an acceleration range 50 g's to 4000 g's.

Figure 3C:
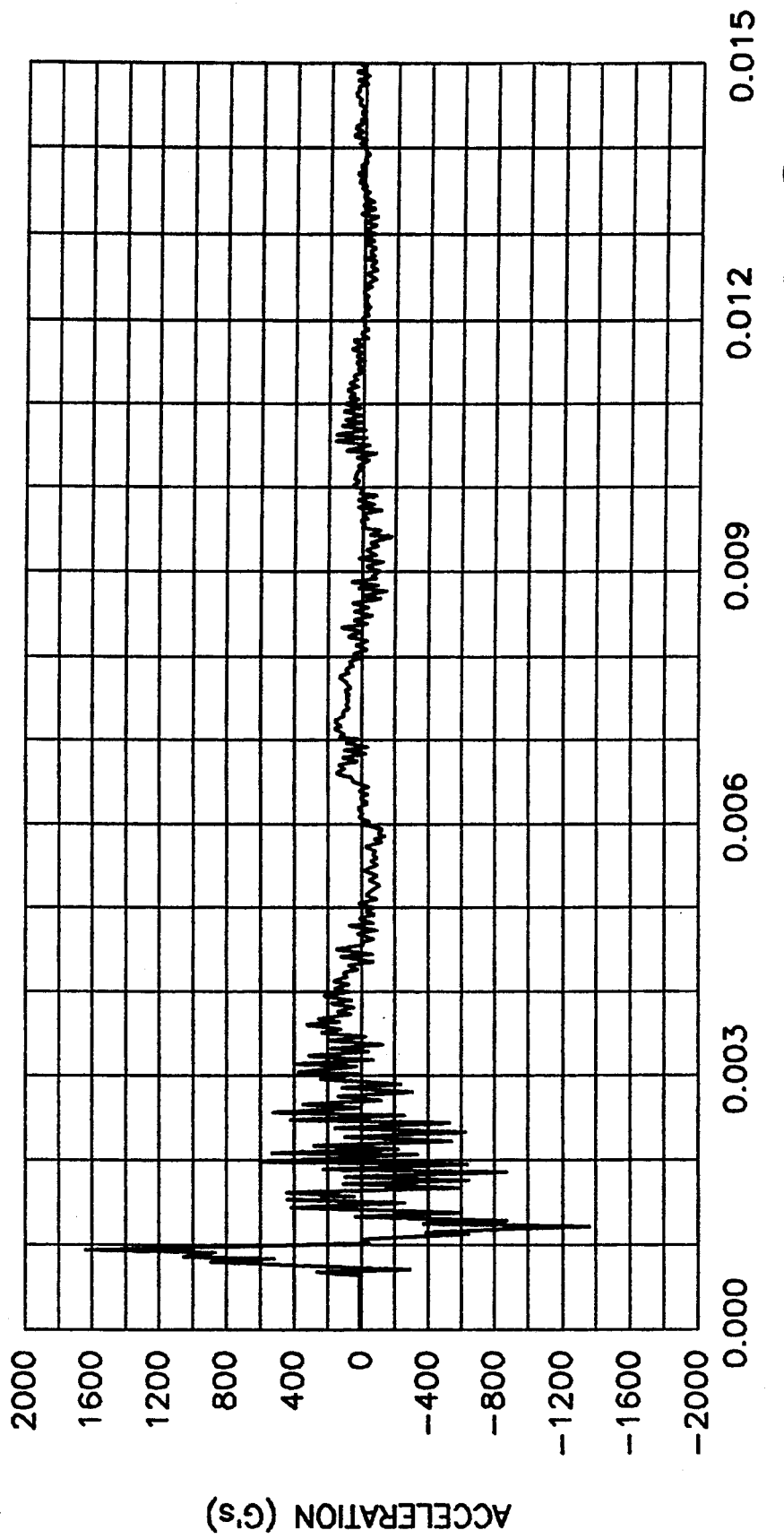
FIG. 3C is a TH profile of the component tested at its top right corner in the z direction.
Figure 3D:
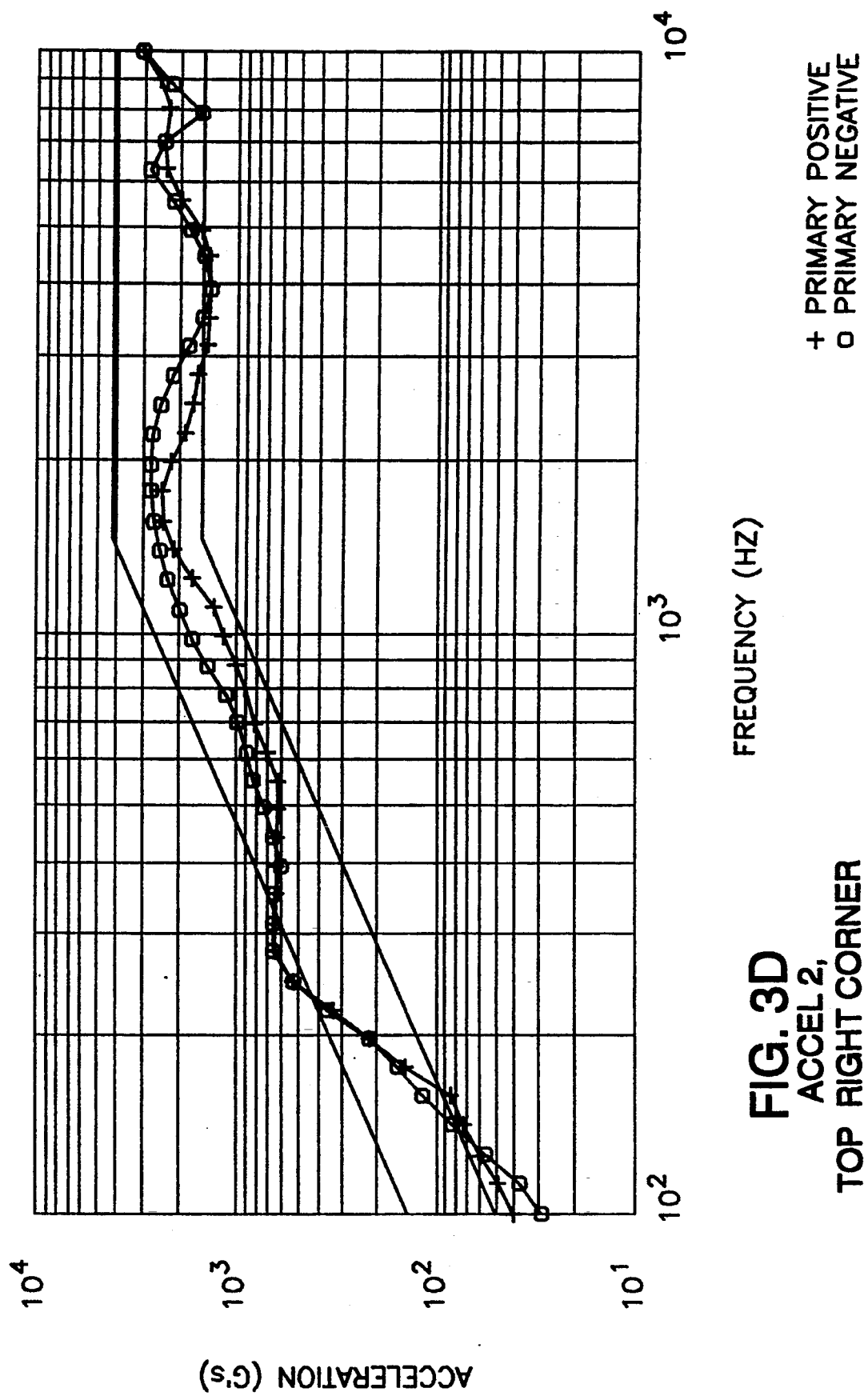
FIG. 3D is a SRS profile of the component tested at its top right corner in the z direction.

FIGS. 3C and 3D, which show accelerometers connected to different points of the test unit than for FIGS. 3A and 3B, demonstrate the frequency and acceleration ranges are essentially constant across the component.

Figure 4A:
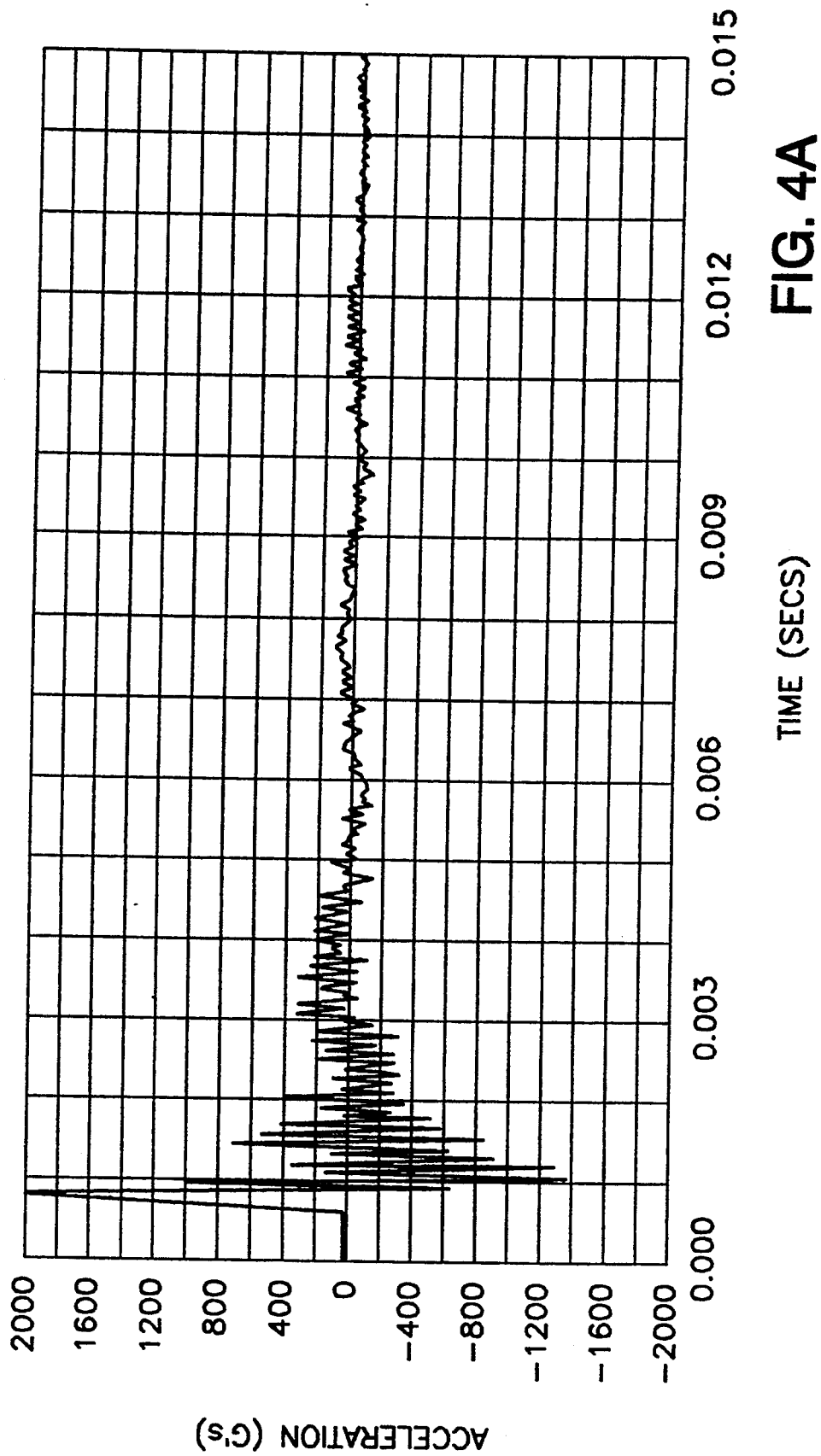
FIG. 4A is a TH profile for the component tested at its right side center in the x direction.
Figure 4B:
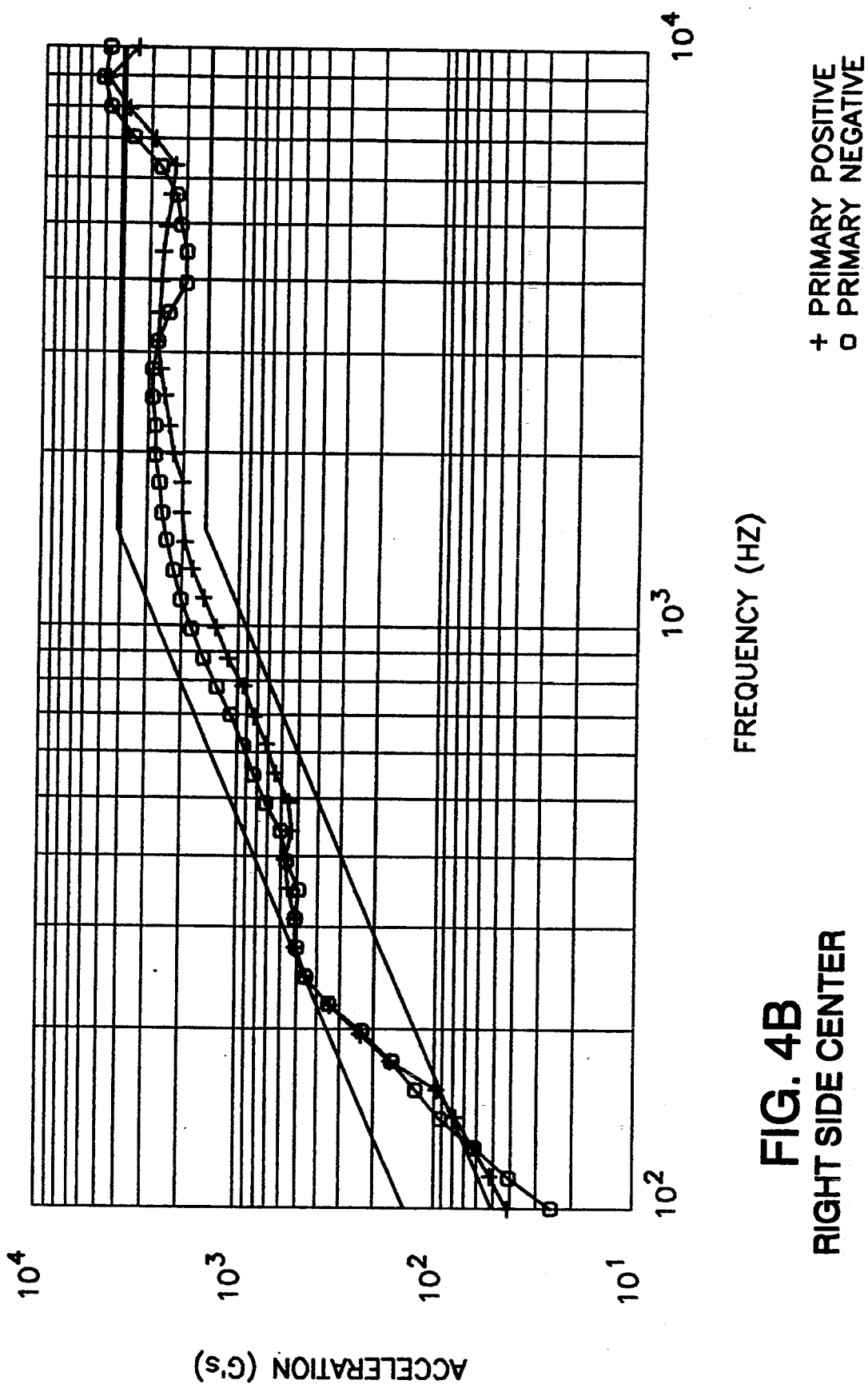
FIG. 4B is a SRS profile of the component tested at its right side center in the x direction.

To perform a shock test on the test unit 48 in the x direction, the fixture 44 is removed and replaced with the fixture 46. The test unit is placed on the fixture 46 so as to receive a shock pulse in the x direction of the test unit which is perpendicular to the path of the hammer. The accelerometer is attached to the right side center of the test unit and steps 3 through 5 of the method followed. The TH and SRS profiles for the shock test in the x direction are shown in FIGS. 4A and 4B. The profiles demonstrate the shock machine of the present invention can provide shock force of 6000 g's over a 100 to 10000 hertz frequency range within the +/−3 db tolerance range.

Figure 5A:
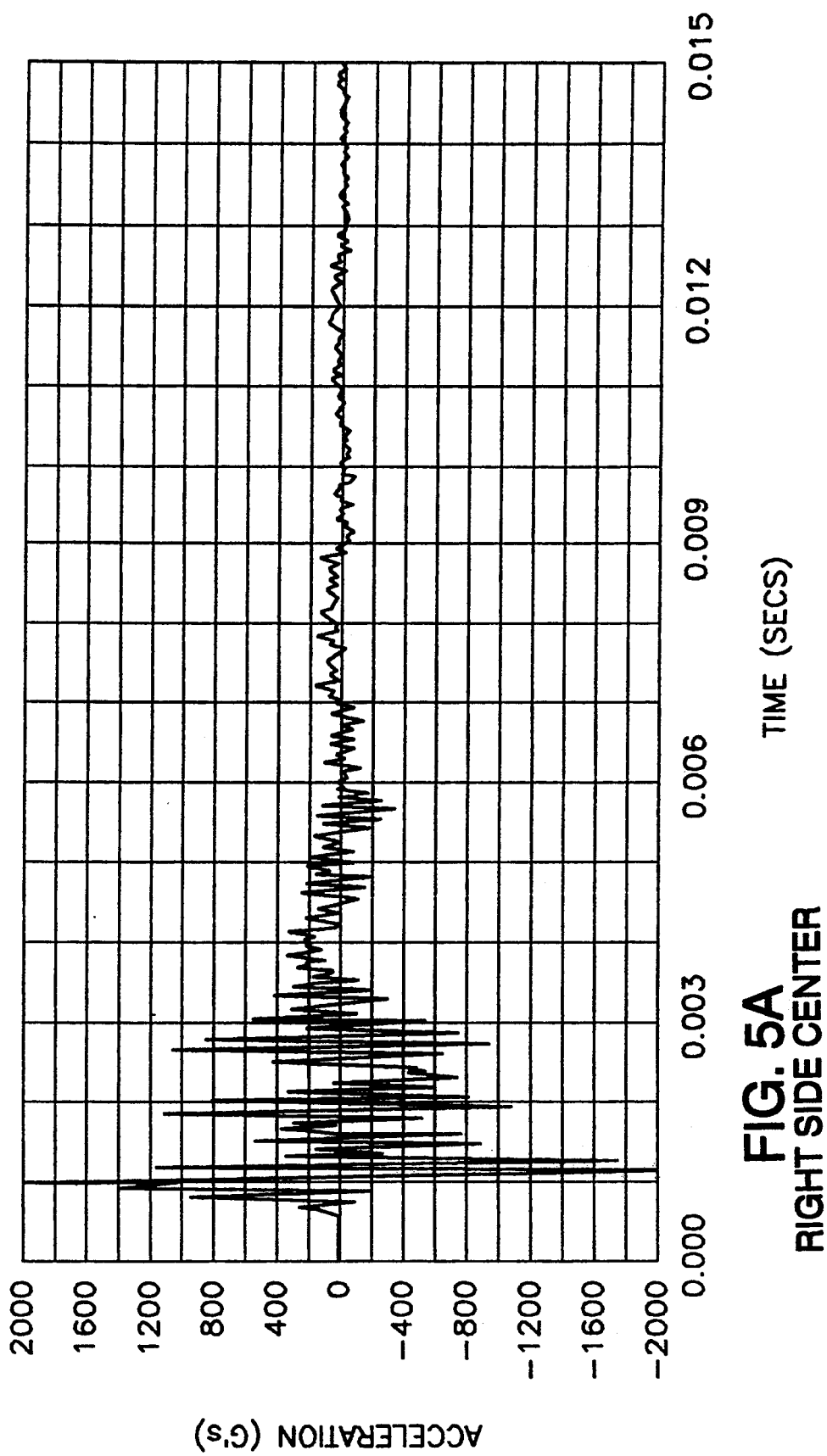
FIG. 5A is a TH profile for the component tested at its right side center in the y direction.
Figure 5B:
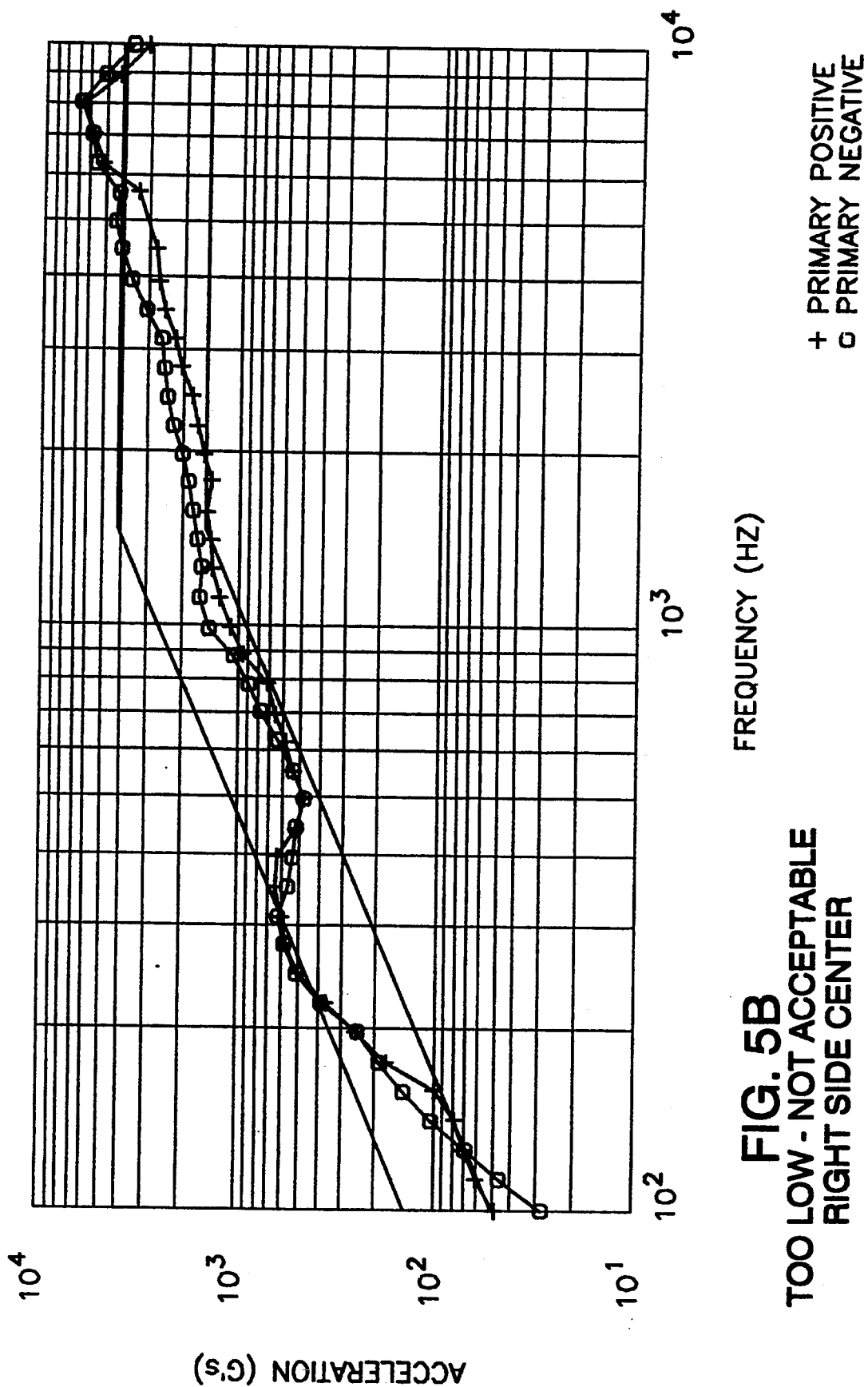
FIG. 5B is a SRS profile for the component tested at its right side center in the y direction.
Figure 6A:
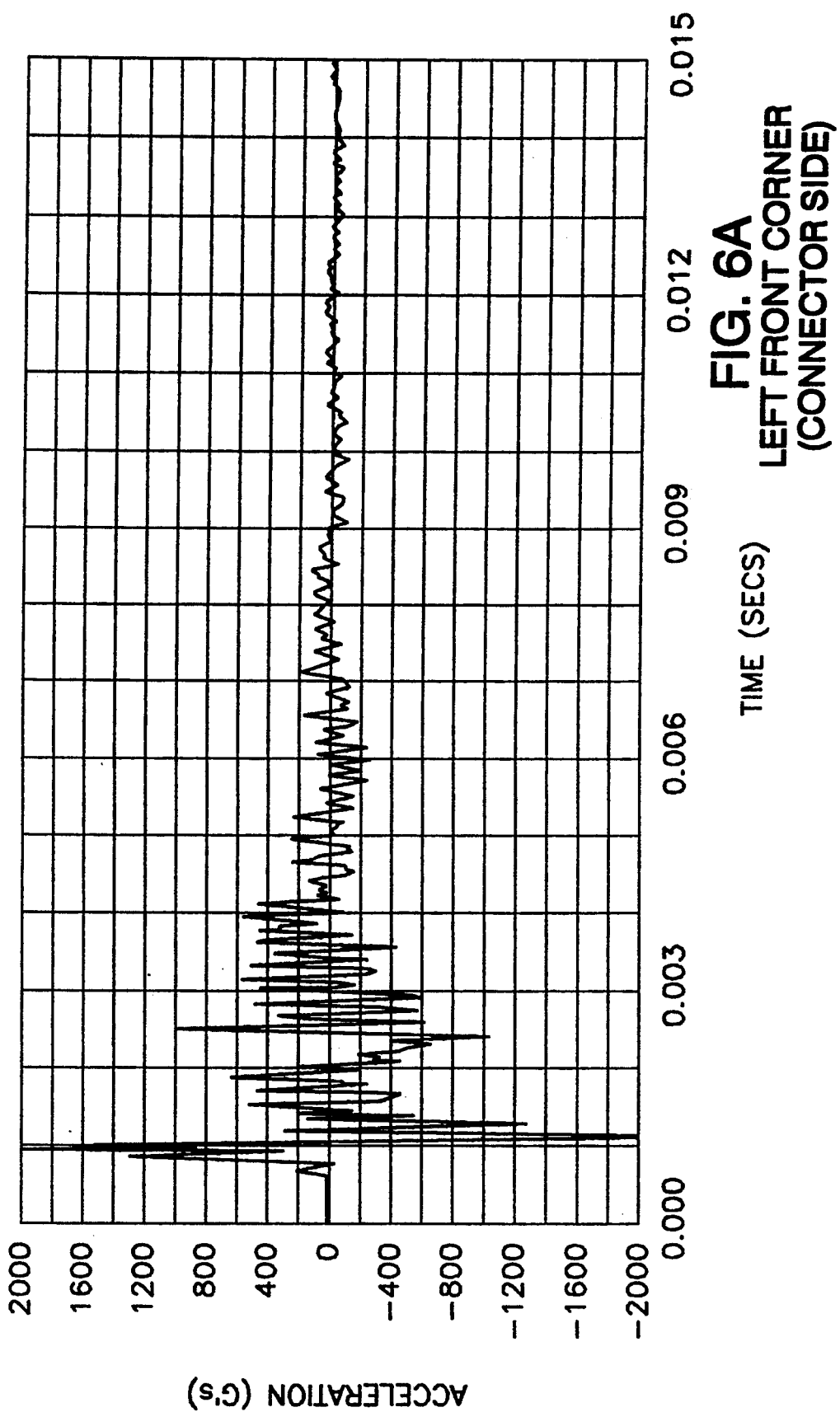
FIG. 6A is a TH profile for the component tested at its left front corner in the y direction.
Figure 6B:
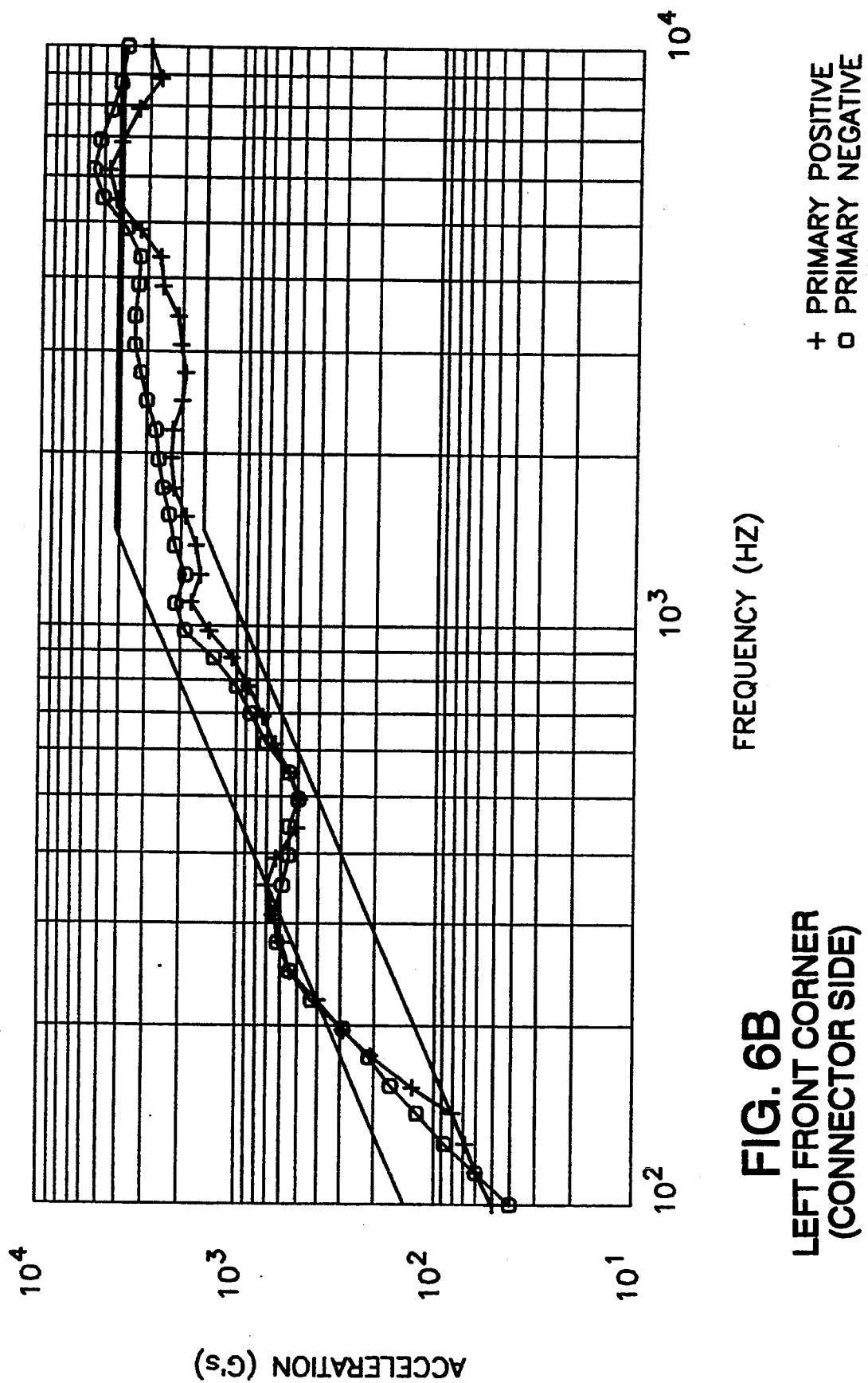
FIG. 6B is a SRT profile for a component tested at its left front corner in the y direction.

To perform a shock test on the test unit in the y direction of the test unit 48, the unit is rotated 90 degrees on the replaceable fixture 46. The accelerometer is attached to the right side center of the component and steps 3-5 repeated for the test method described above. FIGS. 5A and 5B show the frequency and acceleration ranges for the test component. For an acceleration of about 6000 g's a peak frequency of 8000 hertz is achieved before increasing to 10000 hertz at about 3000 g's. FIGS. 6A and 6B show that the accelerations and frequencies are essentially constant across the component when the accelerometers are attached to the left front corner of the test component.

In summary, the required shock response spectrum profile can be controlled by the present invention in several ways. In one instance, the anvil plates 36 can decrease or increase the resonance, depending on how these plates are bolted together. Tightly joining them will raise the resonant frequency. Loosely joining, one may attach spacers or less than a full complement of bolts, will lower the resonant frequency. To achieve damping of the shock pulse, one may change the materials of the anvil. The lower frequencies can be controlled by the number and thickness of the flexure plates. To further control the shock response spectrum, one can select the shape of the impact point. Attaching soft materials to the strike plate can shape the acceleration time history, the softer the interposer, the longer the duration and lower the acceleration level.

While a preferred embodiment of the invention has been shown and described, it will be understood by those skilled in the art that various modifications can be made in the invention without departing from the spirit and scope of the invention.

What is claimed is:

1. A pyrotechnic shock testing machine comprising:
   a) a frame 20;
   b) a hammer;
   c) means 23 attached to the frame for supporting the hammer 28;
   d) anvil means 32 for generating high energy shock forces in response to impact by the hammer;
   e) vertical and horizontal plates means 42 connecting the anvil means 32 to the frame 20, the plate means aligning the frame and anvil in a common vertical plane within the frame for controlling a low frequency response of a shock force applied to the anvil;

f) removable fixture means 44, 46 connected to the anvil means for supporting a test unit 48 for shock testing in an x or y direction relative to the horizontal axis of the frame or z direction relative to the vertical axis of the frame, according to attachment of the test unit 48 to the fixture means 44, 46; and g) measuring means 54 attached to the test unit for recording shock levels incurred by the test unit 48 when the hammer 28 is caused to strike the anvil means 32.

2. The shock testing machine of claim 1 wherein the anvil means comprises a plurality of plates 36 including means to control high frequency response in the range of 500 to 10,000 hertz of a shock wave.

3. The shock testing machine of claim 2 wherein the anvil means comprises a plurality of plates of different metals to achieve damping of a shock pulse.

4. The shock testing machine of claim 3 wherein the number of flexure plate means and materials are selected to control lower frequencies of a shock wave.

5. The shock testing machine of claim 4 wherein the removable fixture is attached to the anvil and adapted to test the test unit in an x or y direction.

6. The method of testing a test unit in a pyrotechnic shock tester having flexure plates and an anvil comprising the steps of:

a) calculating the number, width and thickness of flexure plates for installation in a pyrotechnic shock tester;

b) installing the flexure plates in a tester frame including a pendulum and hammer;

c) selecting the materials and thicknesses of anvil plates for the pyrotechnic shock tester to control low frequency component in the range of 150 to 500 hertz of a shock force applied to the anvil;

d) connecting the anvil to the flexure plates to be in a vertical plane of and within the tester frame and coupling the anvil plates together to control high frequency components in the range of 500 to 10,000 hertz of the shock force applied to the anvil;

e) attaching a replaceable fixture to the anvil for supporting a test unit for testing in a selected x, y, or z direction relative to the hammer path;

f) connecting at least one accelerometer to the test unit;

g) connecting a digital data acquisition and analysis system to receive an output from the accelerometer;

h) elevating the hammer to a selected height in the frame; and i) dropping the hammer to strike the anvil and deliver a pyrotechnic shock wave to the test unit in the selected test direction whereby the TH and SRS profiles of the test unit can be generated by the digital data acquisition and analysis system based on the shock received by the test unit as recorded by the accelerometer.

7. The method of claim 6 wherein the step of connecting the anvil to the flexure plates includes uniformly spacing the flexure plates along the sides of the anvil.

8. The method of claim 6 further comprising the step of using a mechanical calibrating means to set the height relative to a reference plane from which the hammer is dropped to strike the anvil.

9. A protechnic shock machine including a frame an upper member and an anvil support member;

a) a hammer;

b) means for supporting the hammer in the upper member;

c) anvil means for generating high energy shock forces in response to impact by the hammer;

d) vertical and horizontal flexure plates attached to the anvil support member and joined to the anvil for mounting the anvil in a vertical plane within the anvil support member for controlling a low frequency response of a shock force applied to the anvil; and e) removable fixture means connected to the anvil for supporting a test unit for shock testing thereof in an x or y direction relative to the horizontal axis of the frame and in the z direction relative to the vertical axis of the frame.

10. The pyrotechnic shock testing machine of claim 9 further including a calibrating arm attached to the upper member for determining the length of the hammer drop.

11. The pyrotechnic shock testing machine of claim 10 wherein the anvil support means member comprises "I" beam sections arranged in a square configuration, the lower element of the anvil support member being attached to a platform such that the entire frame assembly can be picked up with a pallet truck.

12. The pyrotechnic shock testing machine of claim 11 wherein the anvil means comprises a strike plate joined to a plurality of shock transmission plates, the strike plate and shock transmission plates being bolted together to form an assembly which controls the high frequency components in the range of 500 to 10,000 hertz of a shock force applied to the test unit through the anvil means.

13. The pyrotechnic shock testing machine of claim 12 wherein the number of flexure plates are distributed equally along the sides of the shock transmission plates and control the low frequency components in the range of 150 to 500 hertz of a shock force applied to the test unit through the anvil means.

14. The pyrotechnic shock testing machine of claim 13 wherein the removable fixture means includes a first unit for testing the test unit in an x and y direction, and a second fixture for testing the test unit in a z direction.

15. The pyrotechnic shock testing machine of claim 14 including a platform attached to the frame for transporting the machine.

* * * * *